(12) United States Patent
Date et al.

(10) Patent No.: US 7,709,548 B2
(45) Date of Patent: May 4, 2010

(54) METHOD FOR MANUFACTURING MONOSULFONIUM SALT, CATIONIC POLYMERIZATION INITIATOR, CURABLE COMPOSITION, AND CURED PRODUCT

(75) Inventors: Masashi Date, Kyoto (JP); Hideki Kimura, Kyoto (JP); Shinji Yamashita, Kyoto (JP); Jiro Yamamoto, Kyoto (JP)

(73) Assignee: San-Apro Limited, Kyoto-shi (JP)

( * ) Notice: Subject to any disclaimer, the term of this patent is extended or adjusted under 35 U.S.C. 154(b) by 0 days.

(21) Appl. No.: 12/000,728

(22) Filed: Dec. 17, 2007

(65) Prior Publication Data

US 2008/0108720 A1   May 8, 2008

Related U.S. Application Data

(63) Continuation of application No. 10/562,444, filed as application No. PCT/JP2004/008971 on Jun. 24, 2004.

(30) Foreign Application Priority Data

Jun. 25, 2003   (JP)   ............................. 2003-180712

(51) Int. Cl.
*C08F 2/46* (2006.01)
(52) U.S. Cl. ............................. 522/31; 556/64; 568/13; 568/56
(58) Field of Classification Search ................... 522/31; 568/13, 18, 56, 74; 556/65
See application file for complete search history.

(56) References Cited

U.S. PATENT DOCUMENTS

| | | | |
|---|---|---|---|
| 5,274,148 A * | 12/1993 | Dougherty et al. | ............ 556/64 |
| 5,446,172 A * | 8/1995 | Crivello et al. | ................ 549/62 |
| 5,534,557 A | 7/1996 | Abe et al. | |
| 5,639,903 A | 6/1997 | Takahashi et al. | |
| 5,783,358 A | 7/1998 | Schulthess et al. | |
| 5,798,396 A | 8/1998 | Takahashi et al. | |
| 7,060,858 B2 * | 6/2006 | Date et al. | ..................... 568/18 |
| 7,318,991 B2 * | 1/2008 | Ishihara et al. | ........... 430/270.1 |
| 2004/0030158 A1 | 2/2004 | Date et al. | |

FOREIGN PATENT DOCUMENTS

| | | |
|---|---|---|
| JP | 06-345726 | 12/1994 |
| JP | 08-325225 | 12/1996 |
| JP | 09-012615 | 1/1997 |
| JP | 2002-241363 | 8/2002 |
| JP | 2002-241474 | 8/2002 |
| WO | 94/29271 | 12/1994 |

OTHER PUBLICATIONS

Akhtar et al., Synthesis of aryl-substituted sulfonium salts by the phosphorus pentoxide-methanesulfonic acid promoted condensation of sulfoxides with aromatic compounds, Journal of Organic Chemistry (1990), 55(13), 4222-4225.*

International Search Report mailed Nov. 16, 2004 for PCT Application No. PCT/JP2004/008971.

Akhtar et al., "New Synthesis of Aryl-substituted Sulfonium Salts and Their Applications in Photoinitiated Cationic Polymerization", Chemistry of Materials (1990), 2(6), 732-737.

* cited by examiner

*Primary Examiner*—Porfirio Nazario Gonzalez
*Assistant Examiner*—Chukwuma O Nwaonicha
(74) *Attorney, Agent, or Firm*—Wenderoth, Lind & Ponack, L.L.P.

(57) ABSTRACT

A monosulfonium salt in which very little unreacted raw material remains, which has a purity of at least 96%, and which has one sulfonio group in its molecule is manufactured without a refining step. After (a) an aryl compound, (b) a sulfoxide compound, (c) a dehydrating agent, and (d) a $BF_4$, $PF_6$, $AsF_6$, or $SbF_6$ salt of an alkali metal or an alkaline earth metal are introduced into a reaction system, (e) an inorganic acid is added, so that the aryl compound (a) and the sulfoxide compound (b) are subjected to dehydration condensation.

3 Claims, No Drawings

METHOD FOR MANUFACTURING MONOSULFONIUM SALT, CATIONIC POLYMERIZATION INITIATOR, CURABLE COMPOSITION, AND CURED PRODUCT

This application is a continuation of U.S. application Ser. No. 10/562,444, filed Dec. 27, 2005 now abandoned, which is a national stage application of International application No. PCT/JP2004/008971, filed Jun. 24, 2004.

TECHNICAL FIELD

This invention relates to a method for manufacturing a monosulfonium salt that is useful as a cationic polymerization initiator, and more particularly to a high-purity monosulfonium salt (a sulfonium salt having one sulfonio group per molecule), having an aryl group (aromatic ring), to a cationic polymerization initiator, a curable composition, and a cured product.

BACKGROUND ART $BF_4$, $PF_6$, $AsF_6$ and $SbF_6$ salts of triarylsulfonium are known and commonly used up to now as polymerization initiators of high cationic photopolymerization initiation performance.

However, with methods proposed up to now for manufacturing a sulfonium salt, such as a method in which a sulfide and a sulfoxide are condensed in the presence of a strong organic acid such as methanesulfonic acid or an inorganic acid such as sulfuric acid, and then subjected to double decomposition in an aqueous solution of a $BF_4$, $PF_6$, $AsF_6$ or $SbF_6$ salt of an alkali metal or the like (see Japanese Laid-Open Patent Application S61-100557 and Japanese Laid-Open Patent Application S61-212554, for example), a bis-sulfonium salt having two sulfonio groups per molecule is produced in addition to a monosulfonium salt having only one sulfonio group per molecule.

Bis-sulfonium salts generally have higher photopolymerization initiation performance than monosulfonium salts, but they have low solubility in cationic polymerizable monomers or in dilution solvents that are used as needed, so when a sulfonium salt is added to and dissolved in these in the required concentration, there is the problem that a bis-sulfonium salt may precipitate and settle from the sulfonium salt solution over time.

Also, a cationic polymerizable compound containing a bis-sulfonium salt tends to become more viscous over time, which is a problem in that such compounds cannot be stored for an extended periods.

These problems can be solved by refining the bis-sulfonium salts away from sulfonium salts comprising a mixture of monosulfonium salts and bis-sulfonium salts by some means such as recrystallization from an organic solvent, but the problem with performing such refining is that it greatly diminishes the yield of the desired monosulfonium salt.

In view of this, in an effort to solve the problem of the production of a bis-sulfonium salt encountered with conventional methods for manufacturing a sulfonium salt, the inventors have already proposed a manufacturing method with which a monosulfonium salt is obtained as the main component, that is, a manufacturing method with which the desired sulfonium salt can be obtained directly, with condensing a sulfide and a sulfoxide in the presence of a strong acid such as $HBF_4$, $HPF_4$, $HAsF_4$, or $HSbF_4$ without conducting double decomposition (see Japanese Laid-Open Patent Application 2002-241363).

The prior art published information correlated to the invention of this application are the following.
Japanese Laid-Open Patent Application S61-100557
Japanese Laid-Open Patent Application S61-212554
Japanese Laid-Open Patent Application 2002-241363

DISCLOSURE OF THE INVENTION

With the above method proposed by the inventors, however, the solid or oily product obtained by treatment of a reaction solution (hereinafter referred to as "product") is nearly entirely a monosulfonium salt, and there is only a tiny amount of bis-sulfonium salt, if any, but the purity of the monosulfonium salt is 96% or lower, and unreacted starting material remains as an impurity in an amount of about 4% or larger.

The product obtained by this method can be adequately used in an unmodified form as a polymerization initiator for a photo-cationic polymerization paint, for example, but surprisingly, when a photopolymerization composition containing said product was cured with ultraviolet rays or the like, the curing velocity was decreased by the unreacted starting material in said product, and as a result, the photopolymerization composition is not cured to a sufficient level, and furthermore it was found that this problem does not occur if the residual amount of unreacted starting material did not exceed 4%.

Meanwhile, a product containing unreacted starting material can be refined by recrystallization and washing with a solvent such as ethanol, but a problem with performing this refining is that it lowers the yield of the sulfonium salt by several percent to about 10%.

It is an object of the present invention to provide a method for efficiently manufacturing a monosulfonium salt, by which a high-purity monosulfonium salt, that is, a product in which the residual content of unreacted material does not exceed 4%, can be obtained at a high yield without performing refining by washing and recrystallization, and furthermore can be obtained in the form of a monosulfonium salt solution in a high-boiling point solvent, and to provide a cationic polymerization initiator with excellent solubility in organic solvents, a curable composition with good storage stability, and a cured product.

The present invention is directed to a method of manufacturing a monosulfonium salt expressed by the general formula (1):

[Chemical Formula 1]

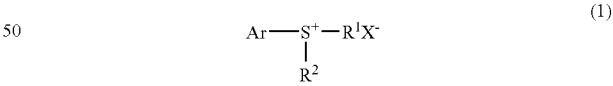

(where Ar is an aryl group that may be substituted; $R^1$ and $R^2$ are each a heterocyclic group or a hydrocarbon group that may be substituted, and may be the same or different; and $X^-$ is $BF_4^-$, $PF_6^-$, $AsF_6^-$, or $SbF_6^-$), wherein (a) an aryl compound, (b) a sulfoxide compound, (c) a dehydrating agent, and (d) a $BF_4$, $PF_6$, $AsF_6$, or $SbF_6$ salt of an alkali metal or an alkaline earth metal are charged into a reaction system, after which (e) an inorganic acid is charged, and the aryl compound (a) and the sulfoxide compound (b) are subjected to dehydration condensation.

More specifically, the method of the present invention for manufacturing a monosulfonium salt is a method for obtaining, at a high purity and yield, the desired monosulfonium salt by charging (a) an aryl compound, (b) a sulfoxide compound, (c) a dehydrating agent, and (d) a $BF_4$, $PF_6$, $AsF_6$, or $SbF_6$ salt of an alkali metal or an alkaline earth metal into a reaction system, then charging (e) an inorganic acid, so that (h) a strong acid, namely, $HBF_4$, $HPF_6$, $HAsF_6$, or $HSbF_6$, is produced by a reaction between (d) the $BF_4$, $PF_6$, $AsF_6$, or $SbF_6$ salt of an alkali metal or an alkaline earth metal and (e) the inorganic acid such as sulfuric acid, and the aryl compound (a) and the sulfoxide compound (b) undergo dehydration condensation at a high reactivity rate in the presence of this strong acid (h) and the dehydrating agent (c).

According to the manufacturing method of the present invention, a high-purity monosulfonium salt with a low unreacted starting material content can be obtained at a high yield. Also, a cationic polymerization initiator composed of a monosulfonium salt obtained by said manufacturing method exhibits excellent solubility in organic solvents in the course of blending in a cationic polymerizable monomer. The blended cationically polymerizable curable composition will have excellent storage stability and curability, and will cure into a material having a good hardness.

Therefore, a sulfonium salt obtained by the manufacturing method of the present invention is favorable as a cationic polymerization initiator for curing cationic polymerizable paints, coating agents, inks, resist films, liquid resists, adhesives, moldable materials, casting materials, putties, glass fiber impregnants, fillers, resins for rapid prototyping and the like with active energy rays such as light, electron beams, or X-rays.

BEST MODE FOR CARRYING OUT THE INVENTION

According to the manufacturing method of the present invention, the aryl compound (a) charged into the reaction system serves to introduce an aryl group (Ar), which can optionally be substituted, into the sulfonium salt expressed by general formula (1).

Examples of this aryl compound (a) include monocyclic or condensed polycyclic unsubstituted aryl compounds, such as benzene, naphthalene, anthracene, phenanthrene, naphthacene, and pyrene; aryl compounds substituted with an alkyl group, such as toluene, cumene, tert-butylbenzene, xylene, ethylbenzene, dodecylbenzene, 1-methylnaphthalene, and 1H-indene; aryl compounds substituted with an aryl group, such as biphenyl, biphenylene, 1,2'-binaphthyl, and 2-phenylnaphthalene; aryl compounds substituted with a nitro group, cyano group, hydroxy group, halogen, or the like, such as nitrobenzene, benzonitrile, phenol, chlorobenzene, and fluorobenzene; aryl compounds substituted with an alkoxy group that may be substituted, such as anisole, ethoxybenzene, 1-methoxynaphthalene, benzyl phenyl ether, and benzofuran; aryl compounds substituted with an aryloxy group which can optionally be substituted, such as diphenyl ether, 2-ethoxynaphthalene, 4-phenoxyphenol, and xanthene; aryl compounds substituted with an alkylsulfonyl group, such as methylphenylsulfone; aryl compounds substituted by an arylsulfonyl group, such as diphenylsulfone; aryl compounds substituted by an acyl group which can optionally be substituted, such as acetophenone, acetylacetophenone, and 2-phenylacetophenone; aryl compounds substituted by an aroyl group which can optionally be substituted, such as benzophenone, 4-methylbenzophenone, and xanthone; aryl compounds substituted by an alkylthio group which can optionally be substituted, such as thioanisole, ethylthiobenzene, benzothiophene, benzylphenyl sulfide, and phenacylphenyl sulfide; aryl compounds substituted by an arylthio group which can optionally be substituted, such as diphenyl sulfide, dibenzothiophene, (2-methylphenyl)phenyl sulfide, (4-methylphenyl)phenyl sulfide, 2,2'-ditolyl sulfide, 2,3'-ditolyl sulfide, 2-phenylthionaphthalene, 9-phenylthioanthracene, (3-chlorophenyl)phenyl sulfide, (4-chlorophenyl) phenyl sulfide, 3,3'-dichlorodiphenyl sulfide, (3-bromophenyl)phenyl sulfide, 2,2'-dibromodiphenyl sulfide, 3,3'-dibromodiphenyl sulfide, (2-methoxyphenyl)phenyl sulfide, phenoxatiin, thioxanthone, 2-isopropylthioxanthone, 2-methoxythioxanthone, 4,4'-diphenylthiobenzophenone, 4,4'-diphenylthiodiphenyl ether, 4,4'-diphenylthiobiphenyl, (4-phenylthiophenyl)phenyl sulfide, (4-benzoylphenyl)phenyl sulfide, (2-chloro-4-benzoylphenyl)phenyl sulfide, and (2-methylthiobenzoylphenyl) phenyl sulfide.

Of these aryl compounds (a), it is preferable to use a monocyclic or condensed polycyclic unsubstituted aryl compounds, an aryl compound substituted by a hydroxy group or a halogen atom, or an aryl compound substituted by an alkyl group, aryl group, alkyloxy group, aryloxy group, acyl group, aroyl group, alkylthio group, or arylthio group, all of which can optionally be substituted themselves, and it is even more preferable to use an unsubstituted aryl compound, an aryl compound substituted by a hydroxyl group or a halogen atom, or an aryl compound substituted with an alkyl group, alkyloxy group, aroyl group, or arylthio group, all of which can optionally be substituted.

Particularly favorable are benzene, phenol, chlorobenzene, fluorobenzene, toluene, tert-butylbenzene, anisole, benzophenone, 4-methylbenzophenone, diphenyl sulfide, (4-chlorophenyl)phenyl sulfide, 2-phenylthionaphthalene, 9-phenylthioanthracene, (4-phenylthiophenyl)phenyl sulfide, 4,4'-diphenylthiobiphenyl, (4-benzoylphenyl)phenyl sulfide, (2-chloro-4-benzoylphenyl)phenyl sulfide, 4,4'-diphenylthiobenzophenone, thioxanthone, and 2-isopropylthioxanthone. These aryl compounds (a) may be used singly or in combinations of two or more types.

With the manufacturing method of the present invention, the sulfoxide compound (b) that is charged into the reaction system is expressed by general formula (2), and forms the sulfonio group in general formula 1 by dehydration condensation with the above-mentioned aryl compound (a).

(2)

$R^1$ and $R^2$ may be the same or different, and are each a heterocyclic group or a hydrocarbon group that may be substituted. Examples of $R^1$ and $R^2$ include methyl group, ethyl group, butyl group, octyl group, and other alkyl groups; cyclopentyl group, cyclohexyl group, and other cycloalkyl groups; phenyl group, naphthyl group, anthryl group, and other aryl groups; and pyridyl group, furfuryl group, and other aromatic heterocyclic groups. $R^1$ and $R^2$ may also be bonded together to form a ring such as a tetramethylene group.

$R^1$ and $R^2$ can optionally be substituted by substituents, examples of which include methyl group, ethyl group, and other alkyl groups; phenyl group, naphthyl group, anthryl group, and other aryl groups; methoxy group and other alkyloxy groups; phenoxy group and other aryloxy groups; methylthio group and other alkylthio groups; phenylthio group and other arylthio groups; acetyl group and other acyl groups, benzoyl group and other aroyl groups; acetoxy group and other acyloxy groups; benzoyloxy group and other aryloxy groups; and cyano group, nitro group, hydroxy group, and halogen atoms.

Specific examples of the sulfoxide compound (b) include dimethyl sulfoxide, methyl ethyl sulfoxide, tetramethylene sulfoxide, diphenyl sulfoxide, dibenzothiophene-5-oxide, (4-methylphenyl)phenyl sulfoxide, 4,4'-dimethyldiphenyl sulfoxide, 4,4'-dimethoxydiphenyl sulfoxide, 4-methylthiodiphenyl sulfoxide, (4-phenylthiophenyl)phenyl sulfoxide, 4,4'-dihydroxydiphenyl sulfoxide, 4,4'-difluorodiphenyl sulfoxide, and 4,4'-dichlorodiphenyl sulfoxide. These sulfoxide compounds (b) may be used singly or in combination of two or more types.

Of the above sulfoxide compounds (b), it is preferable to use a diaryl sulfoxide compound that may be substituted, and particularly diphenyl sulfoxide, 4,4'-dimethyldiphenyl sulfoxide, 4,4'-dimethoxydiphenyl sulfoxide, 4,4'-dihydroxydiphenyl sulfoxide, 4,4'-difluorodiphenyl sulfoxide, or 4,4'-dichlorodiphenyl sulfoxide.

The sulfoxide compound (b) may be a commercially available compound, or one that is synthesized for the specific purpose, and if needed, can be generated within the reaction system by a reaction between a corresponding sulfide compound and hydrogen peroxide or another peroxide.

With the manufacturing method of the present invention, the molar ratio in which the aryl compound (a) and the sulfoxide compound (b) are charged into the reaction system is usually from 1:0.8 to 1:1.2, and preferably from 1:0.9 to 1:1.1. If the sulfoxide compound (b) is used in an amount smaller than 0.8 mol per mole of the aryl compound (a), unreacted aryl compound (a) will remain in an amount of 4% or larger in the product, but in excess of 1.2 moles, unreacted sulfoxide compound (b) will remain in an amount of 4% or larger, and both of these situations result in unsatisfactory curability.

Because the manufacturing method of the present invention involves subjecting the aryl compound (a) and the sulfoxide compound (b) to dehydration condensation, if there is an excess of water in the reaction system, the reaction will be slower and the yield of monosulfonium salt will drop. Accordingly, the dehydrating agent (c) is used for the purpose of removing water from the reaction system.

Examples of the dehydrating agent (c) include phosphorus pentoxide and similar inorganic oxides, polyphosphoric acid and other such inorganic acids, and acetic anhydride, propionic anhydride, phthalic anhydride, and similar organic acid anhydrides. These dehydrating agents (c) may be used singly or in combinations of two or more types. Of these, it is preferable to use acetic anhydride or another organic acid anhydride, with acetic anhydride being particularly preferable.

The dehydrating agent (c) is important in terms of obtaining a sulfonium salt at a high yield, and the amount in which it is used is either the theoretical amount or a slight excess, so that the amount of water in the reaction system during the reaction between (a) and (b) will be not larger than 3%, and preferably not larger than 1%, relative to the overall weight of the reaction system. For instance, when acetic anhydride is used as the dehydrating agent, it is usually used in an amount of 1.0 to 3.0 mol, and preferably 1.0 to 1.5 mol, per mole of water in the reaction system. The "water" in the reaction system implied here includes not only the water in the solvent and inorganic acid (e) being used, but also any water produced by the dehydration condensation of the aryl compound (a) and the sulfoxide compound (b).

With the manufacturing method of the present invention, the $BF_4$, $PF_6$, $AsF_6$, or $SbF_6$ salt of an alkali metal or an alkaline earth metal (d) reacts with the inorganic acid (e) to generate a strong acid (h). A readily available commercial product is preferably used as the $BF_4$, $PF_6$, $AsF_6$, or $SbF_6$ salt of an alkali metal or an alkaline earth metal (d). More specifically, this is a $BF_4$, $PF_6$, $AsF_6$, or $SbF_6$ salt of sodium, potassium, or barium.

Examples of the inorganic acid (e) include sulfuric acid, phosphoric acid, and hydrochloric acid. A strong organic acid such as methanesulfonic acid may be used in place of the inorganic acid (e), but this is undesirable from the standpoint of cost.

It is better to have the concentration of the inorganic acid (e) as high as possible, but it is usually at least 50%, and preferably at least 80%, with 95% or higher being particularly desirable. More specifically, it is preferable to use hydrogen chloride gas, phosphoric acid, or concentrated sulfuric acid with a concentration of at least 98%. Of these, concentrated sulfuric acid is preferable because it is easier to handle.

With the manufacturing method of the present invention, the molar ratio in which the sulfoxide compound (b) and the $BF_4$, $PF_6$, $AsF_6$, or $SbF_6$ salt of an alkali metal or an alkaline earth metal (d) are charged into the reaction system is usually from 1:0.9 to 1:2.0, and preferably from 1:1.0 to 1:1.5. If the alkali metal or alkaline earth metal salt (d) is used in an amount smaller than 0.9 mole per mole of the sulfoxide compound (b), the yield of the targeted monosulfonium salt will be low, but exceeding 2.0 moles increases the cost.

The amounts in which the $BF_4$, $PF_6$, $AsF_6$, or $SbF_6$ salt of an alkali metal or an alkaline earth metal (d) and the inorganic acid (e) are used are usually just the theoretical amounts, but good results will still be obtained when the amount of the inorganic acid (e) is varied between 0.5 and 4 times of the theoretical amount. For instance, the theoretical amounts in the case of a reaction between $NaPF_6$ and sulfuric acid are 1 mole of sulfuric acid per mole of $NaPF_6$, but the amount of sulfuric acid may be varied between 0.5 and 4.0 mole. If the amount of sulfuric acid is smaller than 0.5 mole, the necessary amount of $HPF_6$ may not be generated, but it is also undesirable for the amount of sulfuric acid to exceed 4.0 moles because the aryl compound (a) or the sulfoxide compound (b) will undergo sulfonation and the amount of waste acid will increase.

The manufacturing method of the present invention may be conducted in the presence of a solvent if necessary. Examples of the solvent used in this case include diethyl ether and other ethers; dichloromethane and other chlorine-based organic solvents; methanol, ethanol, and other alcohols; acetone and other ketones; acetic acid and other organic acids; acetic anhydride, propionic anhydride, and other organic acid anhydrides; and acetonitrile and other polar organic solvents. These solvents may be used singly or in combinations of two or more types.

Of the above solvents, it is preferable to use an ether such as diethyl ether; chlorine-based organic solvent such as dichloromethane; organic acid such as acetic acid; organic acid anhydride such as acetic anhydride and propionic anhydride; or polar organic solvent such as acetonitrile. Diethyl ether, dichloromethane, acetic acid, acetic anhydride, and acetonitrile are particularly preferable.

The above solvent may be added along with the other materials prior to the addition of the inorganic acid (e), or may be added at the same time as the inorganic acid (e), or after the inorganic acid (e).

The amount in which the above solvent is used is usually 0 to 80%, and preferably 20 to 60%, relative to the total mass of the aryl compound (a), the sulfoxide compound (b), the dehydrating agent (c), the $BF_4$, $PF_6$, $AsF_6$, or $SbF_6$ salt of an alkali metal or an alkaline earth metal (d), the inorganic acid (e), and said solvent.

With the manufacturing method of the present invention, the order in which the starting materials are charged into the system is important in order to obtain the monosulfonium salt in a high purity. As discussed above for the prior art, with a conventional method (see Japanese Laid-Open Patent 2002-241363) with which a relatively large amount of monosulfonium salt can be manufactured, that is, with a method in which, for example, a dehydrating agent and a solvent are charged into the system, and the sulfoxide compound and the $BF_4$, $PF_6$, $AsF_6$, or $SbF_6$ salt of an alkali metal or an alkaline earth metal are uniformly mixed, followed by the addition of the inorganic acid to generate a strong acid, and then the aryl compound is added dropwise and reacted, the content of the monosulfonium salt in the product thus obtained is 96% or lower, and unreacted starting materials remain in an amount that may inhibit photo-cationic polymerization.

In contrast, with the manufacturing method of the present invention, the aryl compound (a), the sulfoxide compound (b), the dehydrating agent (c), and the $BF_4$, $PF_6$, $AsF_6$, or $SbF_6$ salt of an alkali metal or an alkaline earth metal (d) are charged into the reaction system, after which the inorganic acid (e), preferably concentrated sulfuric acid, is added dropwise to subject the aryl compound (a) and the sulfoxide compound (b) to dehydration condensation.

With this manufacturing method, no inorganic acid (e), such as sulfuric acid, that could bring about a side reaction of the aryl compound (a) or the sulfoxide compound (b) is present in the reaction system at the outset, and the inorganic acid (e) that is added dropwise is immediately consumed for the generation of the strong acid (h). Furthermore, this strong acid (h) is immediately used in the dehydration condensation of the aryl compound (a) and the sulfoxide compound (b). As a result, side reactions of the aryl compound (a) and the sulfoxide compound (b) are suppressed, and a monosulfonium salt can be obtained in a higher purity and higher yield.

With the manufacturing method of the present invention, the amount in which the monosulfonium salt is contained in the resulting product is usually at least 96%, and in most cases at least 97%, and the amount of remaining unreacted starting materials, that is, the aryl compound (a) and/or the sulfoxide compound (b), is usually not larger than 4.0%, and in most cases not larger than 3.0%. If the amount of aryl compound (a) or sulfoxide compound (b) that remains in unreacted form is larger than 4.0%, as mentioned above, there will be a decrease in photocurability when the final product is blended with a cationic polymerizable monomer and used as a curable composition, and another problem is that the resulting cured product will not have a sufficient hardness.

Upon closer scrutiny, an extremely small amount of bis-sulfonium salt may sometimes be produced with the manufacturing method of the present invention, but the amount would never be larger than 1%.

With the manufacturing method of the present invention, the reaction temperature during the dehydration condensation of the aryl compound (a) and the sulfoxide compound (b) is usually somewhere between −30° C. and 120° C., and preferably between 0 and 100° C., with a range of 20 to 80° C. being particularly preferable.

The reaction time will vary with the reaction temperature, reaction concentration, and the intensity of stirring, but is usually between 0.5 and 24 hours, and preferably 1 to 10 hours, after the addition of the inorganic acid (e).

With the manufacturing method of the present invention, the dehydrating agent (c) and the organic acid anhydride, acetic acid, diethyl ether, or other substance used as a solvent can be easily recovered, if necessary, by distillation under normal or reduced pressure after the dehydration condensation of the aryl compound (a) and the sulfoxide compound (b). The temperature at which the dehydrating agent (c) and the solvent are recovered is usually from 40 to 120° C., and preferably from 50 to 80° C. If the temperature is over 120° C., there is the risk that the targeted sulfonium salt will decompose, but under 40° C. there is a risk that there will be a decrease in the recovery of the dehydrating agent (c) or solvent. The recovered dehydrating agent or solvent can be reused.

With the manufacturing method of the present invention, the method for the recovery of the targeted sulfonium salt from the reaction solution obtained by the dehydration condensation of the aryl compound (a) and the sulfoxide compound (b) depends on the properties of the sulfonium salt that is obtained, but this recovery can be accomplished, for instance, by first adding water to the reaction solution, or adding the reaction solution to water, so as to isolate the monosulfonium salt in the form of a solid or an oily substance, and then dissolving the monosulfonium salt with an organic solvent (f) having a boiling point of 100° C. or lower, such as dichloromethane, methyl ethyl ketone, or ethyl acetate. In this case, the water and the organic solvent (f) having a boiling point of 100° C. or lower may jointly be added at the same time to the reaction solution. After this, the organic layer in which the monosulfonium salt is dissolved is washed with water and, if necessary, neutralized with an aqueous caustic soda solution or the like, after which the organic solvent (f) having a boiling point of 100° C. or lower is distilled off, for example, which gives a product whose monosulfonium salt content is at least 96% and the amount of unreacted aryl compound (a) and/or sulfoxide compound (b) is 4.0% or lower.

If the targeted monosulfonium salt is to be obtained in the form of a solution, then, as discussed above, water is added to the reaction solution, or the reaction solution is added to water, so as to isolate the monosulfonium salt in the form of a solid or an oily substance, and this product is then dissolved by adding the organic solvent (f) having a boiling point of 100° C. or lower, the resulting organic layer is, if necessary, neutralized with an aqueous caustic soda solution, washed with water, and then dried with anhydrous sodium sulfate, calcium chloride, or the like. However, a problem with a solution of such a low boiling-point solvent such as this is that, when a cationic polymerizable curable composition containing this solution is applied to a metal sheet or the like and cured with light, the cured coating film gives off a solvent odor.

Consequently, the solvent used for obtaining a monosulfonium salt as a solution is usually an organic solvent (g) having a boiling point of 150° C. or higher, preferable examples of which include propylene carbonate, carbitol, carbitol acetate, and γ-butyrolactone. Of these, propylene carbonate and γ-butyrolactone are particularly preferable because they are cationically polymerizable.

Following is an example of how the targeted monosulfonium salt can be obtained as a solution of an organic solvent (g) having a boiling point of 150° C. or higher. Water and an organic solvent (f) having a boiling point of 100° C. or lower are charged, either at the same time or the water first, into a reaction system obtained by the dehydration condensation of the aryl compound (a) and the sulfoxide compound (b), the organic layer thus obtained is neutralized and washed, and then the organic solvent (g) having a boiling point of 150° C. or higher is added, and the organic solvent (f) is distilled off under normal or reduced pressure, usually at a temperature of 120° C. or lower. The organic solvent (g) having a boiling point of 150° C. or higher may be gradually added while the organic solvent (f) with a boiling point of 100° C. or lower is being distilled off, or may be added at the same time as the organic solvent (f) having a boiling point of 100° C. or lower is added to the reaction system. This method enables omission of the step conventionally undertaken, in which the target substance is first separated in the form of a solid or an oily substance, and then redissolved in a high-boiling solvent.

The monosulfonium salt concentration when the monosulfonium salt obtained with the present invention is obtained as a solution of an organic solvent (g) having a boiling point of 150° C. or higher is usually from 35 to 75%, and preferably 40 to 70%.

The monosulfonium salt obtained by the manufacturing method of the present invention is used as a cationic polymerization initiator. In this case, the monosulfonium salt of the present invention may be used singly or as a combination of two kinds or more, or may be used together with another cationic polymerization initiator.

Any other cationic polymerization initiator can be used, provided that the compound generates a strong acid through the action of heat or active energy rays, but examples include known substances such as sulfonium salts, iodonium salts, phosphonium salts, and pyridinium salts, and iron-allene complexes. When a different cationic polymerization initiator is used, it is used in an amount of 1 to 200 mass parts (hereinafter referred to as parts), and preferably 5 to 100 parts, per 100 parts of the monosulfonium salt obtained by the present invention.

Examples of the above-mentioned sulfonium salts that can be used as a different cationic polymerization initiator include triphenylsulfonium hexafluorophosphate, 4-di-(p-toluoyl)sulfonio-4'-tert-butylphenylcarbonyl-diphenyl sulfide hexafluorophosphate, 4-di-(p-toluoyl)sulfonio-4'-tert-butylphenylcarbonyl-diphenyl sulfide hexafluoroantimonate, 7-di-(p-toluoyl)sulfonio-2-isopropyl-thioxanthone hexafluorophosphate, and 7-di-(p-toluoyl)sulfonio-2-isopropyl-thioxanthone hexafluoroantimonate, as well as the aromatic sulfonium salts disclosed in Japanese Laid-Open Patent Applications H7-61964 and H8-165290 and U.S. Pat. Nos. 4,231,951 and 4,256,828.

Bis(4-diphenylsulfonio)-phenyl)sulfide bishexafluorophosphate, bis(4-diphenylsulfonio)-phenyl)sulfide bishexafluoroantimonate, or another such bissulfonium salt can also be used in combination as a sulfonium salt. However, if these are used in too large an amount, there may be a decrease of the solubility in solvents or cationic polymerizable monomers, or an increase over time in the viscosity of the blend in admixture with a cationic polymerizable monomer. When these bissulfonium salts are used in combination, they are usually used in an amount of not exceeding 100 parts, and preferably not exceeding 20 parts, and even more preferably not exceeding 5 parts, per 100 parts monosulfonium salt.

Examples of the above-mentioned iodonium salts that can be used as other cationic polymerization initiators include diphenyliodonium hexafluorophosphate, diphenyliodonium hexafluoroantimonate, and bis(dodecylphenyl)iodonium tetrakis(pentafluorophenyl)borate, as well as the aromatic iodonium salts disclosed in Japanese Laid-Open Patent Application H6-184170 and U.S. Pat. No. 4,256,828.

Examples of the above-mentioned phosphonium salts that can be used as a different cationic polymerization initiator include tetraphenylphosphonium hexafluorophosphate and tetraphenylphosphonium hexafluoroantimonate, as well as the aromatic phosphonium salts disclosed in Japanese Laid-Open Patent Application H6-157624.

Examples of the above-mentioned pyridinium salts that can be used as the different cationic polymerization initiator include the pyridinium salts disclosed in Japanese Patent Publication 2519480 and Japanese Laid-Open Patent Application H5-222112.

The curable composition of the present invention, which can be cured by light, electron beams, X-rays, or other active energy rays, can be obtained by blending the cationic polymerization initiator of the present invention, consisting of the monosulfonium salt obtained by the manufacturing method of the present invention, with a cationically polymerizable compound.

Examples of the cationically polymerizable compounds with which the cationic polymerization initiator of the present invention can be blended include epoxy compounds, vinyl ether compounds, oxetane compounds, styrene and other ethylenically unsaturated compounds, and spiro-ortho esters, bicyclo-ortho esters, and other cyclic ethers.

Examples of the above-mentioned epoxy compounds include phenyl glycidyl ether, p-tert-butylglycidyl ether, butylglycidyl ether, 2-ethylhexyl glycidyl ether, allyl glycidyl ether, 1,2-butylene oxide, 1,3-butadiene monoxide, 1,2-dodecylene oxide, epichlorohydrin, 1,2-epoxydecane, ethylene oxide, propylene oxide, styrene oxide, cyclohexene oxide, 3-methacryloyloxymethylcyclohexene oxide, 3-vinylcyclohexene oxide, 4-vinylcyclohexene oxide, and other monofunctional epoxy compounds; and 1,1,3-tetradecadiene dioxide, limonene dioxide, 3,4-epoxycyclohexylmethyl-(3,4-epoxycyclohexyl)carboxylate, di(3,4-epoxycyclohexyl) adipate, bisphenol A-type epoxy resins, bisphenol F-type epoxy resins, phenol novolac-type epoxy resins, o-, m-, and p-cresol novolac-type epoxy resins, polyhydric alcohol polyglycidyl ethers, polybutadiene glycol diglycidyl ethers, copolymers of methyl methacrylate, 2-ethylhexyl methacrylate, or another (meth)acrylate and glycidyl methacrylate, and other polyfunctional epoxy compounds.

Examples of the above-mentioned vinyl ether compounds include methyl vinyl ether, ethyl vinyl ether, butyl vinyl ether, isobutyl vinyl ether, cyclohexyl vinyl ether, 2-chloroethyl vinyl ether, 2-phenoxyethyl vinyl ether, 2-hydroxyethyl vinyl ether, 4-hydroxybutyl vinyl ether, stearyl vinyl ether, 2-acetoxyethyl vinyl ether, diethylene glycol monovinyl ether, 2-ethylhexyl vinyl ether, dodecyl vinyl ether, octadecyl vinyl ether, and other such alkyl vinyl ether compounds; allyl vinyl ether, 2-methacryloyloxyethyl vinyl ether, 2-acryloyloxyethyl vinyl ether, and other alkenyl vinyl ether compounds; phenyl vinyl ether, p-methoxyphenyl vinyl ether, and other aryl vinyl ether compounds; N-vinylcarbasol, N-vinylpyrrolidone, and other cationic polymerizable nitrogen-containing compounds; and butanediol-1,4-divinyl ether, triethylene glycol divinyl ether, 1,4-benzenedivinyl ether, hydroquinone divinyl ether, cyclohexanedimethanol divinyl ether, diethyleneglycol divinyl ether, dipropylene glycol divinyl ether, hexanediol divinyl ether, and other polyfunctional vinyl ether compounds.

Examples of the above-mentioned oxetane compounds include 3-ethyl-3-hydroxymethyloxetane, 1,4-[(3-ethyl-3-oxetanylmethoxy)methyl]benzene, 3-ethyl-3-(phenoxymethyl)oxetane, di[1-ethyl(3-oxetanyl)]methyl ether, 3-ethyl-3-(2-ethylhexylmethyl)oxetane, 3-ethyl-3-{[3-(triethoxysilyl)propoxy]methyl}oxetane, oxetanylsilsesquioxetane, and phenol novolac oxetane.

Examples of the above-mentioned bicyclo-ortho esters include 1-phenyl-4-ethyl-2,6,7-trioxabicyclo[2,2,2]octane and 1-ethyl-4-hydroxymethyl-2,6,7-trioxabicyclo[2,2,2]octane.

Examples of the above-mentioned spiro-ortho carbonate compounds include 1,5,7,11-tetraoxaspiro[5,5]undecane, 3,9-dibenzyl-1,5,7,11-tetraoxaspiro[5,5]undecane, 1,4,6-trioxaspiro[4,4]nonane, 2-methyl-1,4,6-trioxaspiro[4,4]nonane, and 1,4,6-trioxaspiro[4,5]decane.

These cationically polymerizable compounds can be used singly, or two or more can be used together. The cationic polymerization initiator of the present invention is particularly preferable for curing epoxy compounds, oxetane compounds, and vinyl ether compounds.

A proper blending proportion of the cationic polymerization initiator of the present invention and the cationically polymerizable compound is such that 0.01 to 20 parts or, preferably, 0.1 to 10 parts of the cationic polymerization initiator are taken per 100 parts of the cationic polymerizable compound but should be selected by taking into consideration the factors such as the nature of the cationically polymerizable compound, types and irradiation dose of the actinic rays and desired curing time as well as the temperature and humidity during curing, thickness of the coating film and others.

The cationic polymerization initiator of the present invention can be prepared as a solution of a solvent, such as one of the solvents listed as examples of the organic solvent (g) having a boiling point of 150° C. or higher, in order to facilitate dissolution into the cationically polymerizable compound.

If needed, a conventional sensitizer can be used in combination with the cationically polymerization initiator of the present invention. Examples of such known sensitizers include anthracene, 9,10-dibutoxyanthracene, phenylcyclohexyl ketone, thioxanthone, phenothiazine, chlorothioxanthone, xanthone, diphenylanthracene, rubrene, carbazole, naphthol, perylene, and derivatives of these.

When one of these sensitizers is used, the amount of addition is 5 to 100 parts, or preferably 10 to 50 parts, per 100 parts of the cationic polymerization initiator of the present invention.

The curable composition of the present invention is obtained by dissolving, under heating if necessary, the cationic polymerization initiator of the present invention in a cationically polymerizable compound. The curable composition of the present invention is usually used in the form of a clear liquid, but depending on its application, pigments, dyes, fillers, antistatic agents, flame retardants, anti-foaming agents, flow regulators, antioxidants, and others may be dissolved in the composition or mixed in with a sand mill, three-roller mill, or other mixing means.

The curable composition of the present invention can be cured into a solvent-insoluble form or a tack-free condition within from 0.1 second to a few minutes by irradiation with light (such as ultraviolet light or visible light) or an electron beam, X-rays, gamma rays, or other active energy rays. Any light source can be used for this curing, insofar as it has sufficient energy to induce decomposition of the cationic polymerization initiator, but it is preferable to use UV light or visible light from a low-pressure mercury lamp, medium-pressure mercury lamp, high-pressure mercury lamp, ultra-high-pressure mercury lamp, metal halide lamp, xenon lamp, or carbon arc lamp, or sunlight. A semiconductor laser, argon laser, He—Cd laser, or other laser light sources may also be used. The exposure time to the energy rays will vary with the intensity of the energy rays, but usually about 0.1 second to 10 seconds is sufficient. However, relatively thick coatings are preferably irradiated for longer than this. If necessary, heating may be performed to promote the cationic polymerization reaction.

The curable composition of the present invention can be applied to metals, woods, rubbers, plastics, glass, ceramics, and other materials by a roll coater, spin coater, sprayer, brush, printer, or the like, and then irradiated with active energy rays to obtain a cured product of the present invention.

Specific examples of applications of the curable composition of the present invention include paints, coating agents, inks, resist films, liquid resists, adhesives, molding materials, casting materials, putties, glass fiber impregnants, fillers, and photolithographic resins.

EXAMPLES

The present invention will now be described further by way of working examples, but is not limited to or by these.

Example 1

4.28 g (23.3 mmol) of potassium hexafluorophosphate ($KPF_6$), 10 ml of acetonitrile, 3.61 g (19.4 mmol) of diphenyl sulfide, 4.05 g (20.0 mmol) of diphenyl sulfoxide, and 5.94 g (58.2 mmol) of acetic anhydride were introduced into a 100 ml reaction vessel and uniformly mixed, and then 2.28 g (23.3 mmol) of concentrated sulfuric acid was added dropwise at room temperature over a period of 60 minutes. Heat was generated during this course to increase the temperature, but the system was cooled so that the temperature did not exceed 40° C. After 1 hour of stirring at 40° C., the system was cooled to room temperature, and 20 ml of water were added and stirred for 10 minutes, whereupon an oily substance became separated. 20 ml of ethyl acetate were added to this to dissolve the oily substance, and the organic layer was taken. This organic layer was washed with 10 ml of 20% caustic soda and washed three times with 10 ml of water, and then the acetonitrile and ethyl acetate were distilled off under reduced pressure to give 9.72 g (97% yield) of a slightly yellowish solid.

This substance was analyzed by $^{13}C$-NMR, IR, and HPLC (using a Model L-7000 high-performance liquid chromatograph made by Hitachi), which revealed that the product contained 98.0% (4-phenylthiophenyl)diphenylsulfonium hexafluorophosphate, 0.8% thiodi-p-phenylenebis(diphenylsulfonium)bishexafluorophosphate, and 0.5% diphenyl sulfide and 0.7% diphenyl sulfoxide as unreacted starting materials.

Example 2

3.91 g (23.3 mmol) of sodium hexafluorophosphate ($NaPF_6$), 8 ml of acetonitrile, 3.61 g (19.4 mmol) of diphenyl sulfide, 4.05 g (20.0 mmol) of diphenyl sulfoxide, and 5.94 g (58.1 mmol) of acetic anhydride were introduced into a 100 ml reaction vessel and uniformly mixed, and then 2.28 g (23.3 mmol) of concentrated sulfuric acid were added dropwise at a temperature of 40° C. or lower over a period of 40 minutes. After 2 hours of stirring at 40° C., the system was cooled to room temperature, and 20 ml of water and 20 ml of ethyl acetate were added and stirred for 10 minutes, and the organic layer was taken. This organic layer was washed with 10 ml of water while the pH of the aqueous layer was adjusted to between 7 and 8 with 40% caustic soda, and then the organic layer was washed two more times with 10 ml of water. 10 g of propylene carbonate were added to this organic layer, and then the acetonitrile and ethyl acetate were distilled off under reduced pressure at 100° C. or lower, to give 19.4 g (97% yield) of a pale yellow solution with a solids content of 50%.

This substance was analyzed by $^{13}$C-NMR, IR, and HPLC, to reveal that the solution contained 50.1% propylene carbonate, and the balance of 49.9% was made up of 97.7% (4-phenylthiophenyl)diphenylsulfonium hexafluorophosphate, 0.8% thiodi-p-phenylenebis(diphenylsulfonium)bishexafluorophosphate, and 0.8% diphenyl sulfide and 0.7% diphenyl sulfoxide as the unreacted starting materials.

Example 3

10.12 g (96% yield) of a slightly yellowish solid were obtained in the same manner as in Example 1, except that the diphenyl sulfoxide was replaced with 4.61 g (20.0 mmol) of 4,4'-dimethyldiphenyl sulfoxide.

This product was analyzed by $^{13}$C-NMR, IR, and HPLC, which revealed it to contain 99.1% (4-phenylthiophenyl)-4,4'-dimethyldiphenylsulfonium hexafluorophosphate, 0.4% thiodi-p-phenylenebis(4,4'-dimethyldiphenylsulfonium) bishexafluorophosphate, and 0.2% diphenyl sulfide and 0.3% 4,4'-dimethyldiphenyl sulfoxide as unreacted starting materials.

Example 4

11.37 g (96% yield) of a slightly yellowish solid were obtained in the same manner as in Example 1, except that the diphenyl sulfide was replaced with 5.63 g (19.4 mmol) of 4-benzoyldiphenyl sulfide.

This product was analyzed by $^{13}$C-NMR, IR, and HPLC, which revealed it to contain 98.6% [4-(4-benzoylphenyl)thiophenyl]-diphenylsulfonium hexafluorophosphate, and 0.8% 4-benzoyldiphenyl sulfide and 0.6% diphenyl sulfoxide as the unreacted starting materials.

Example 5

9.42 g (97% yield) of a slightly yellowish solid were obtained in the same manner as in Example 1 except that the amount of the diphenyl sulfoxide was changed to 3.80 g (18.8 mmol).

This substance was analyzed by $^{13}$C-NMR, IR, and HPLC which revealed the product to contain 98.0% (4-phenylthiophenyl)diphenylsulfonium hexafluorophosphonate, 0.5% thiodi-p-phenylenebis(diphenylsulfonium)bishexafluorophosphate, and 1.2% diphenyl sulfide and 0.3% diphenyl sulfoxide as the unreacted starting materials.

Example 6

11.31 g (96% yield) of a light yellow solid were obtained in the same manner as in Example 1 except that the potassium hexafluorophosphate was replaced with 5.86 g (21.3 mmol) of potassium hexafluoroantimonate (KSbF$_6$) and the amount of the concentrated sulfuric acid was changed to 2.08 g (21.3 mmol).

This product was analyzed by $^{13}$C-NMR, IR, and HPLC, which revealed it to contain 98.5% (4-phenylthiophenyl)diphenylsulfonium hexafluoroantimonate, 0.8% thiodi-p-phenylenebis(diphenylsulfonium)bishexafluoroantimonate, and 0.4% diphenyl sulfide and 0.36% diphenyl sulfoxide as the unreacted starting materials.

Example 7

22.6 g (96% yield) of a light yellow solution of a 50% solid content was obtained in the same manner as in Example 2, except that the sodium hexafluorophosphate (NaPF$_6$) was replaced with 5.52 g (21.3 mmol) of sodium hexafluoroantimonate (NaSbF$_6$), and the amount of the concentrated sulfuric acid was changed to 2.08 g (21.3 mmol).

This product was analyzed by $^{13}$C-NMR, IR, and HPLC, which revealed the solution to contain 49.8% propylene carbonate, and the balance 50.2% was made up of 98.2% (4-phenylthiophenyl)diphenyl-sulfonium hexafluoroantimonate, 1.0% thiodi-p-phenylenebis(diphenyl-sulfonium)bishexafluoroantimonate, and 0.2% diphenyl sulfide and 0.6% diphenyl sulfoxide as the unreacted starting materials.

Example 8

11.07 g (97% yield) of a slightly yellowish solid were obtained in the same manner as in Example 1, except that the diphenyl sulfoxide was used in an amount of 3.80 g (18.8 mmol), the potassium hexafluorophosphate was replaced with 5.86 g (21.3 mmol) of potassium hexafluoroantimonate (KSbF$_6$), and the amount of the concentrated sulfuric acid was changed to 2.08 g (21.3 mmol).

This product was analyzed by $^{13}$C-NMR, IR, and HPLC, which revealed it to contain 98.9% (4-phenylthiophenyl) diphenylsulfonium hexafluoroantimonate, 0.4% thiodi-p-phenylenebis(diphenylsulfonium)bishexafluoroantimonate, and 0.5% diphenyl sulfide and 0.2% diphenyl sulfoxide as the unreacted starting materials.

Comparative Example 1

5.36 g (29.1 mmol) of potassium hexafluorophosphate (KPF$_6$) and 5.36 g of acetic acid were introduced into a 100 ml reaction vessel and stirred and mixed, and then 2.91 g (29.1 mmol) of concentrated sulfuric acid were added, and the system was stirred for 30 minutes.

4.05 g (20.0 mmol) of diphenyl sulfoxide, 3.61 g (19.4 mmol) of diphenyl sulfide, and 5.94 g (58.1 mmol) of acetic anhydride were uniformly dissolved, and the resulting solution was added dropwise to the above solution at room temperature, and the system was stirred for 30 minutes. The system was then aged for 1 hour at 75° C., and then the solvent, mainly composed of acetic acid, was removed by distillation under reduced pressure at the same temperature.

This reaction solution was cooled to room temperature, after which 20 mL of dichloromethane and 20 ml of water were added and stirred to effect liquid separation. The organic layer thus obtained was washed three times with 10 mL of water, after which the dichloromethane was distilled off, to give 9.62 g (96% yield) of a slightly yellowish solid.

This product was analyzed by $^{13}$C-NMR, IR, and HPLC, which revealed it to contain 94.0% (4-phenylthiophenyl) diphenylsulfonium hexafluorophosphate, 0.8% thiodi-p-phenylenebis(diphenylsulfonium)bishexafluorophosphate, and 2.2% diphenyl sulfide and 3.0% diphenyl sulfoxide as the unreacted starting materials.

Comparative Example 2

10 ml of ethanol were added to 3.0 g of the solid obtained in Comparative Example 1, and the system was heated and stirred, followed by cooling to room temperature to precipitate crystals. These crystals were collected by filtration and dried, to give 2.2 g (70% yield) of a white powder.

This white powder was analyzed by $^{13}$C-NMR, IR, and HPLC, which revealed it to contain 99.4% (4-phenylthiophenyl)diphenylsulfonium hexafluorophosphate, 0.4% thiodi-p- phenylenebis(diphenylsulfonium)bishexafluorophosphate, and 0.1% diphenyl sulfide and 0.1% diphenyl sulfoxide as the unreacted starting materials.

Comparative Example 3

8.12 g (93% yield) of a slightly yellowish solid were obtained in the same manner as in Comparative Example 1, except that potassium hexafluorophosphate (KPF$_6$) was used in an amount of 2.86 g (17.0 mmol), and concentrated sulfuric acid was used in an amount of 1.70 g (17.0 mmol).

This solid was analyzed by $^{13}$C-NMR, IR, and HPLC, which revealed it to contain 83.3% (4-phenylthiophenyl)diphenylsulfonium hexafluorophosphate, 1.0% thiodi-p-phenylenebis(diphenylsulfonium)bishexafluorophosphate, and 6.7% diphenyl sulfide and 9.0% diphenyl sulfoxide as the unreacted starting materials.

Comparative Example 4

10.72 g (92% yield) of a slightly yellowish solid were obtained in the same manner as in Comparative Example 1, except that the potassium hexafluorophosphate (KPF$_6$) was replaced with 5.86 g (21.3 mmol) of sodium hexafluoroantimonate (NaSbF$_6$).

This solid was analyzed by $^{13}$C-NMR, IR, and HPLC, which revealed it to contain 93.0% (4-phenylthiophenyl)diphenylsulfonium hexafluoroantimonate, 1.0% thiodi-p-phenylenebis(diphenylsulfonium)bishexafluoroantimonate, and 3.0% diphenyl sulfide and 3.0% diphenyl sulfoxide as the unreacted starting materials.

Comparative Example 5

3.0 g of the solid obtained in Comparative Example 3 were heated and dissolved in 10 ml of ethanol, and the solution was then cooled to room temperature to precipitate crystals. These crystals were filtered off and dried, which gave 2.0 g (64% yield) of a white powder.

This white powder was analyzed by $^{13}$C-NMR, IR, and HPLC, which revealed it to contain 99.4% (4-phenylthiophenyl)diphenylsulfonium hexafluoroantimonate, 0.4% thiodi-p-phenylenebis(diphenylsulfonium)bishexafluoroantimonate, and 0.2% diphenyl sulfide as the unreacted starting materials, without diphenyl sulfoxide being detected.

Comparative Example 6

By using UVI-6990 (a product by Dow Co.) as a cationic polymerization initiator, which was a commercially available propylene carbonate solution of a mixture of (4-phenylthiophenyl) diphenylsulfonium hexafluorophosphate and thiodi-p-phenylenebis (diphenylsulfonium)bishexafluorophosphate, the following comparative evaluation was undertaken.

This initiator had a solid content of 44.0%, and the HPLC analysis revealed the solid to contain 25.4% of (4-phenylthiophenyl)diphenylsulfonium hexafluorophosphate, 61.4% thiodi-p-phenylenebis(diphenylsulfonium)bishexafluorophosphate, and 13.2% of unidentifiable compounds.

Comparative Example 7

UVI-6974 (a product by Dow Co.), which is a commercially available propylene carbonate solution of a mixture of (4-phenylthiophenyl)diphenylsulfonium hexafluoroantimonate and thiodi-p-phenylenebis(diphenylsulfonium)bishexafluoroantimonate, was used as a cationic polymerization initiator in the following comparative evaluation.

This initiator had a solids content of 49.8%, and HPLC analysis revealed the solids to contain 28.7% (4-phenylthiophenyl)diphenylsulfonium hexafluoroantimonate, 63.5% thiodi-p-phenylenebis(diphenylsulfonium)bishexafluoroantimonate, and 7.8% unidentifiable compounds.

The products obtained in Examples 1 to 8 and Comparative Examples 1 to 5, as well as the commercially available cationic polymerization initiators of Comparative Examples 6 and 7 were each blended into an alicyclic epoxy resin (a cationically polymerizable compound), and the curability test described below was conducted, the results of which are given in Table 1. It can be seen from these results that the monosulfonium salts obtained by the present invention have good epoxy resin curing effect and afforded a high pencil hardness of the cured coating film, as compared with commercial products that were mixtures of a bissulfonium salt and a monosulfonium salt, which are usually said to provide higher photopolymerization initiation performance than a monosulfonium salt.

TABLE 1

| Test Ex. | Product | Type of anion | Monosulfonium salt content (%) | Unreacted starting material content (%) | Curing rate (sec) | Cured film hardness |
|---|---|---|---|---|---|---|
| 1 | Example 1 | PF$_6^-$ | 98.0 | 1.2 | 130 | 2H |
| 2 | Example 2 | PF$_6^-$ | 97.7 | 1.5 | 135 | 2H |
| 3 | Example 3 | PF$_6^-$ | 99.1 | 0.5 | 125 | 2H |
| 4 | Example 4 | PF$_6^-$ | 98.6 | 1.4 | 130 | 2H |
| 5 | Example 5 | PF$_6^-$ | 98.0 | 1.5 | 125 | 2H |
| 6 | Comparative Example 1 | PF$_6^-$ | 94.0 | 5.2 | 225 | H |
| 7 | Comparative Example 2 | PF$_6^-$ | 99.4 | 0.2 | 125 | 2H |
| 8 | Comparative Example 3 | PF$_6^-$ | 83.3 | 15.7 | 430 | HB |
| 9 | (Comparative Example 6) | PF$_6^-$ | 25.4 | unknown | 120 | 3H |
| 10 | Example 6 | SbF$_6^-$ | 98.5 | 0.7 | 170 | 3H |
| 11 | Example 7 | SbF$_6^-$ | 98.2 | 0.8 | 175 | 3H |
| 12 | Example 8 | SbF$_6^-$ | 98.9 | 0.7 | 165 | 3H |
| 13 | Comparative Example 4 | SbF$_6^-$ | 93.0 | 6 | 240 | 2H |
| 14 | Comparative Example 5 | SbF$_6^-$ | 99.4 | 0.2 | 165 | 3H |
| 15 | (Comparative Example 7) | SbF$_6^-$ | 28.7 | unknown | 165 | 3H |

Curability Testing Method 10 parts of the product obtained in each of Examples 1, 3 to 6, and 8 and Comparative Examples 1 to 5 was added to 10 parts propylene carbonate, and the mixture was heated to prepare a 50% propylene carbonate solution. For Examples 2 and 7, the 50% propylene carbonate solution obtained was used as it is.

(1) Test Examples 1 to 9

5 parts of a 50% propylene carbonate solution of the product obtained in each of Examples 1 to 5 and Comparative Examples 1 to 3 (main component: monosulfonium PF$_6$ salt) was mixed with 100 parts of UVR-6110 (trade name of a cationic polymerizable compound made by UCC, 3,4-epoxycyclohexylmethyl-3,4-epoxycyclohexane carboxylate (alicyclic epoxy resin) to prepare a mixture. In Test Example 9, 5 parts of the commercially available cationic polymerization initiator (PF$_6$ salt) mentioned in Comparative Example 6 was mixed with 100 parts UVR-6110 to prepare a mixture.

(2) Test Examples 10 to 15

1 part of a 50% propylene carbonate solution of the product obtained in each of Examples 6 to 8 and Comparative Examples 4 and 5 (main component: monosulfonium SbF$_6$ salt) was mixed with 100 parts UVR-6110 (supra) to prepare a mixture. In Test Example 15, 1 part of the commercially available cationic polymerization initiator (SbF$_6$ salt) mentioned in Comparative Example 7 was mixed with 100 parts UVR-6110 to prepare a mixture.

Using a #16 bar coater, each of the above liquid mixtures was applied to a polyester film (80 μm thick) in a coating film thickness of about 35 μm. This coating film was cured with light under the following conditions, and the curing rate and pencil hardness of the cured film was evaluated.

Conditions
  Ultraviolet irradiation apparatus: belt conveyor type of UV irradiation apparatus (made by Eye Graphics)
  Lamp: metal halide lamp (120 W/cm, 1.5 kW, irradiation distance: 18 cm)
  Irradiation: conveyor speed of 4.5 m/minute, 1 pass through the UV irradiation apparatus (1) Curing Rate Test A polyester film coated with the above-mentioned mixture was placed on the conveyor moving at the above-mentioned speed, and irradiated with UV rays. After this, the curing rate was evaluated from the time it took for the pencil hardness of the cured film to reach HB ("curing time" in Table 1). The shorter is this time, the faster the curing, that is, the better the performance of the sulfonium salt as a photopolymerization initiator.

(2) Hardness Test of Cured Films

The above-mentioned cured coating film was kept standing at room temperature, after which the pencil hardness at the point when the coating film hardness stabilized ("Cured film hardness" in Table 1) was measured. The higher is the pencil hardness, the better is the polymerization of the cationically photopolymerizable monomer.

Solubility Test

Test Examples 16 and 17

20 parts of a propylene carbonate solution of the cationic polymerization initiators used in each of Test Examples 5 and 9 was added to 100 parts of various kinds of organic solvent, and the dissolution appearance was evaluated. These results are given in Table 2.

Evaluation Criteria
  A: clearent and uniform solution
  B: very slightly cloudy
  C: cloudy or separation into two layers

TABLE 2

| | Test Example | |
|---|---|---|
| | 16 | 17 |
| | Product | |
| | Example 5 | (Comparative Example 6) |
| Ethyl acetate | A | C |
| Methanol | A | C |
| Methylene chloride | A | B |
| Chloroform | A | A |
| Tetrahydrofuran | A | A |
| Acetone | A | A |
| Methyl ethyl ketone | A | A |
| Methyl isobutyl ketone | A | C |

Storage Stability Test

As an acceleration test for storage stability, a mixture of the cationic polymerization initiator solution and a cationic polymerizable compound was evaluated by measuring its change in the viscosity when stored at a temperature of 80° C.

Test Examples 18 and 19

5 parts of a propylene carbonate solution of the cationic polymerization initiators used in each of Test Examples 5 and 9 was added to 100 parts UVR-6110 (the alicyclic epoxy resin, supra), and 200 g of this mixture was put in a 250 mL brown plastic bottle and stored in an 80° C. thermostat.

Test Examples 20 and 21

3 parts of a propylene carbonate solution of the cationic polymerization initiator used in each of Test Examples 12 and 15 were mixed with 100 parts UVR-6110, and 200 g of this mixture taken in a 250 ml brown plastic bottle and stored in an 80° C. thermostat.

The above-mentioned mixture was adjusted to 25° C. in a thermostatic tank that had been adjusted to 25° C., and the viscosity of the mixture was measured at the start of storage and after one, two, four, and six weeks. These results are given in Table 3. As seen in the results, the smaller the increase in the viscosity, the more stable the cationic polymerizable composition, and the longer it can be stored.

TABLE 3

| | | | Viscosity after storage for (mPa·s) | | | | |
|---|---|---|---|---|---|---|---|
| Test Ex. | Product | Anion | At start | 1 week | 2 weeks | 4 weeks | 6 weeks |
| 18 | Example 5 | PF$_6^-$ | 480 | 480 | 480 | 500 | 500 |
| 19 | (Comparative Example 6) | PF$_6^-$ | 485 | 485 | 550 | 610 | 650 |
| 20 | Example 8 | SbF$_6^-$ | 470 | 470 | 470 | 510 | 650 |
| 21 | (Comparative Example 7) | SbF$_6^-$ | 480 | 920 | 4000 | 42000 | not measurable |

Reference Example

In the above test examples, the tendency was such that the more unreacted starting materials there were contained in the product whose main component was a monosulfonium salt, the lower was the pencil hardness of the cured film and, in particular, the UV curing rate for a mixture of this product and a cationic polymerizable compound.

In view of this, to ascertain systematically the effect of unreacted starting materials, small amounts of diphenyl sulfide and diphenyl sulfoxide were added either singly or both in combination to a mixture of UVR-6110 (supra) and a propylene carbonate solution of the product of Test Example 1, and the influences of the unreacted starting materials (diphenyl sulfide and diphenyl sulfoxide) on the curing rate of the mixture and the cured film hardness were examined. These results are given in Table 4.

The added amount (w) of diphenyl sulfide and diphenyl sulfoxide was such that the total (y) of this added amount (w) and the amount (x) of unreacted starting materials present in the product as prepared was 3%, 4%, or 6% relative to the total of the amount (z) of produced mixed into the UVR-6110 at the outset and the added amount (w) of diphenyl sulfide and diphenyl sulfoxide.

The liquid mixture used for the curability test was prepared by mixing 3 parts of a 50% propylene carbonate solution of a cationic polymerization initiator in 100 parts UVR-6110.

Curability was evaluated by coating a polyester film with the mixture and irradiating it with UV light, then measuring the time it took for the pencil hardness of the coating film to reach HB (the curing time in Table 4), and the pencil hardness of the coating film after 10 minutes of UV irradiation (the "Coating film hardness after 10 minutes" in Table 4), under the conditions given for curability test method above. Reference Examples 1 and 10 given the evaluation results for the case where the products of Test Examples 1 and 8 were used, respectively.

TABLE 4

| | Added parts (w) | | | Curability test | |
|---|---|---|---|---|---|
| Ref. Ex. | Diphenyl sulfoxide | Diphenyl sulfide | [y × 100]/ [w + Z] % | Curing time (sec.) | Cured film hardness after 10 min. |
| 1 | 0 | 0 | 1.2 | 170 | H |
| 2 | 0.047 | 0 | 3.0 | 180 | H |
| 3 | 0 | 0.050 | 3.1 | 185 | H |
| 4 | 0.075 | 0 | 4.1 | 240 | HB |
| 5 | 0 | 0.073 | 4.0 | 225 | HB |
| 6 | 0.030 | 0.047 | 4.1 | 240 | HB |
| 7 | 0.129 | 0 | 6.0 | >600 | B |
| 8 | 0 | 0.128 | 6.0 | >600 | B |
| 9 | 0.064 | 0.071 | 6.2 | >600 | B |
| 10 | 0 | 0 | 15.7 | >600 | 3B |

It can be seen from the results in Table 4 that if the amount of remaining sulfide and sulfoxide as the unreacted starting materials is equal to or larger than 4.0% of the total amount of these and the sulfonium salt, cationic polymerization will be slower and there will be a decrease in the hardness of the cured film.

The invention claimed is:

1. A method for manufacturing a monosulfonium salt represented by the general formula (1):

wherein Ar denotes an optionally substituted aryl group; each of $R^1$ and $R^2$ denotes the same or different, optionally substituted heterocyclic group or hydrocarbon group; and $X^-$ denotes $BF_4^-$, $PF_6^-$, $AsF_6^-$, or $SbF_6^-$, which comprises introducing (a) an aryl compound, (b) a sulfoxide compound, (c) a dehydrating agent, and (d) a $BF_4$, $PF_6$, $AsF_6$, or $SbF_6$ salt of an alkali metal or an alkaline earth metal into a reaction system, followed by introduction of (e) an inorganic acid so that the aryl compound (a) and the sulfoxide compound (b) are subjected to dehydration condensation.

2. The manufacturing method described in claim 1, wherein (e) the inorganic acid is sulfuric acid.

3. The manufacturing method described in claim 1, wherein (f) an organic solvent having a boiling point not higher than 100° C. and (g) an organic solvent having a boiling point of 150° C. or higher are added to the reaction solution obtained by the dehydration condensation of the aryl compound (a) and the sulfoxide compound (b), followed by removal of the organic solvent (f) added to said reaction solution by distillation.

* * * * *